United States Patent
He et al.

(10) Patent No.: US 8,692,551 B2
(45) Date of Patent: Apr. 8, 2014

(54) MAGNETIC RESONANCE IMAGING WATER-FAT SEPARATION METHOD

(75) Inventors: Qiang He, Shenzhen (CN); De He Weng, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 363 days.

(21) Appl. No.: 13/097,311

(22) Filed: Apr. 29, 2011

(65) Prior Publication Data

US 2011/0267054 A1    Nov. 3, 2011

(30) Foreign Application Priority Data

Apr. 30, 2010    (CN) .......................... 2010 1 0160444

(51) Int. Cl.
*G01V 3/00*    (2006.01)
(52) U.S. Cl.
USPC .......................................... 324/309; 324/318
(58) Field of Classification Search
USPC .............................. 324/300–322; 600/407–445
See application file for complete search history.

(56) References Cited

U.S. PATENT DOCUMENTS

| | | | | |
|---|---|---|---|---|
| 6,774,624 B2 * | 8/2004 | Anderson et al. | ........ | 324/207.17 |
| 6,980,921 B2 * | 12/2005 | Anderson et al. | ............. | 702/150 |
| 7,096,148 B2 * | 8/2006 | Anderson et al. | ............. | 702/134 |
| 7,301,342 B2 * | 11/2007 | Moriguchi et al. | ........... | 324/309 |
| 7,619,411 B2 * | 11/2009 | Reeder | ........................ | 324/312 |
| 7,835,779 B2 * | 11/2010 | Anderson et al. | ............. | 600/407 |
| 8,278,924 B2 * | 10/2012 | Fuderer | ........................ | 324/307 |
| 2003/0184285 A1 * | 10/2003 | Anderson et al. | ........ | 324/207.17 |
| 2011/0267054 A1 * | 11/2011 | He et al. | ........................ | 324/309 |
| 2011/0274331 A1 * | 11/2011 | Weng | ........................... | 382/131 |
| 2012/0301000 A1 * | 11/2012 | Bornert et al. | ................ | 382/130 |
| 2013/0265052 A1 * | 10/2013 | Nickel | .......................... | 324/309 |

OTHER PUBLICATIONS

"Motion Correction with Propeller MRI: Application to Head Motion and Free-Breathing Cardiac Imaging," Pipe, Magnetic Resonance in Medicine, vol. 42 (1999) pp. 963-969.
"Three-Point Dixon Technique for True Water/Fat Decomposition with B0 Inhomogeneity Correction," Glover et al., Magnetic Resonance in Medicine, vol. 18, (1991) pp. 371-383.
"Nonuniform Fast Fourier Transforms Using Min-Max Interpolation," Fessler et al., IEEE Trans. on Signal Processing, vol. 51, No. 2 (2003) pp. 560-574.
Matlab Code of NUFFT, Index of/~fessler/irt/irt.
U.S. Appl. No. 13/097,245, filed Apr. 29, 2011.

* cited by examiner

Primary Examiner — Brij Shrivastav
(74) Attorney, Agent, or Firm — Schiff Hardin LLP

(57) ABSTRACT

A magnetic resonance imaging (MRI) water-fat separation method includes acquiring in-phase image raw measurement data and out-of-phase image raw measurement data with an MRI device, reconstructing an in-phase image and an out-of-phase image according to a system matrix and the raw measurement data using the penalty function regularized iterative reconstruction method, and calculating water and fat images according to the in-phase image and the out-of-phase image. The use of the penalty function regularized iterative method eliminates the need for k-space raw measurement data with a 100% sampling rate, thereby reducing the MRI scan time, shortening the entire imaging time, and improving the efficiency of the MRI device.

11 Claims, 5 Drawing Sheets

MAGNETIC RESONANCE IMAGING WATER-FAT SEPARATION METHOD

BACKGROUND OF THE INVENTION

1. Field of the Invention

The present invention relates to the magnetic resonance imaging (MRI) technical field, and more particularly to an MRI water-fat separation method, wherein k-space raw measurement data are acquired based on the under-sampling method.

2. Description of the Prior Art

In magnetic resonance imaging (MRI), the body's molecular environment for hydrogen protons in fat tissue is different from that for hydrogen protons in other tissues, which results in a difference in the resonance frequency of the protons. The relaxation time of the hydrogen protons in fat tissue and those in other tissues is also different when they are excited by radio frequency pulses at the same time. When signals are collected at different echo times, the fat tissue and non-fat tissues show different phases and signal strengths.

The Dixon method is known for use to generate pure water proton images in magnetic resonance imaging, and its basic principle is: acquiring the in-phase and out-of-phase echo signals of the water and fat protons respectively, and calculating two signals with different phases to create one pure water proton image and one pure fat proton image respectively. Inhibiting fat in water proton images is thereby achieved.

There are many k-space data collecting methods that can be used in conjunction with the Dixon method in this field, for example, Cartesian trajectory acquisition (sampling), and radial or spiral trajectory sampling. Cartesian trajectory sampling refers to sampling k-space data along a Cartesian path (trajectory), and generating the coordinate space image using Fast Fourier Transform (FFT), and calculating the water and fat images according to the image data acquired in this manner. The single-point Dixon method, two-point Dixon method and three-point and multiple-point Dixon methods are easy and timesaving, but they are sensitive to motion artifacts, and the spin echo sequence is also sensitive to motion artifacts, so there are usually motion artifacts in the images obtained by the Dixon method based on the Cartesian trajectory sampling.

In the radial or spiral trajectory sampling methods, k-space data are sampled along the non-Cartesian trajectory, such as radial trajectory or spiral trajectory. Based on this sampling method, the phase correction and chemical shift correction can be carried out in the image field and k-space to avoid blurred reconstructed images. The advantage of this kind of methods is that the motion introduces fuzziness rather than artifacts into the reconstructed image, which has little impact on identifying the objects in the image, but using the radial or spiral trajectory sampling usually increases the image calculation complexity and takes much more time.

As mentioned above, the Cartesian trajectory sampling method is easy and timesaving, but it is very sensitive to motion such as rigid motion and pulsation. The radial or spiral trajectory sampling methods convert the motion artifact into fuzziness in the reconstructed image, but the calculation is complex and it takes much more time. In short, neither of the two methods above can eliminate rigid motion artifacts.

In Chinese patent application, "A Magnetic Resonance Imaging Method Achieving Water-fat Separation", filed on the same date with this application, a method of magnetic resonance imaging is disclosed that uses BLADE trajectory to collect the raw measurement data of one in-phase image and two out-of-phase images, and performs phase correction for the raw measurement data of the out-of-phase image using the raw measurement data of the in-phase image when reconstructing the out-of-phase image, thus eliminating the motion artifacts in the water and fat images obtained from calculation.

However, when using the conventional BLADE trajectory acquisition, an in-phase image and two out-of-phase images are first reconstructed through a gridding reconstruction method, and then the water-fat separation calculation is carried out. However, the gridding reconstructing method needs a high sampling rate (usually 100% sampling rate) to eliminate the strip artifacts, so it needs a longer scan time to acquire k-space raw measurement data, which causes the entire imaging to take longer and reduces the efficiency of the MRI device.

SUMMARY OF THE INVENTION

An object of the present invention is to provide an MRI water-fat separation method to reduce the MRI scan time and to improve the efficiency of the MRI device.

This object is achieved in accordance with the present invention by an MRI water-fat separation method, which includes:

Acquiring in-phase image raw measurement data and out-of-phase image raw measurement data with an MRI device;

Reconstructing the in-phase image and out-of-phase image according to a system matrix and the raw measurement data using a penalty function regularized iterative reconstruction method;

Calculating water and fat images according to the in-phase image and out-of-phase image.

Preferably, this method uses an under-sampling method to collect the raw measurement data.

In the technical solution above, the under-sampling spiral trajectory, radial trajectory, Cartesian trajectory or BLADE trajectory are used to collect the raw measurement data.

Preferably, this method collects the raw measurement data of one in-phase image and two out-of-phase images, and reconstructs one in-phase image and two out-of-phase images.

In the technical solution above, the method first acquires two out-of-phase echoes, and then acquires one in-phase echo; or, first acquires one in-phase echo, and then acquires two out-of-phase echoes; or, first acquires one out-of-phase echo, and then acquires one in-phase echo, and then acquires the other out-of-phase echo.

The method further includes: generating the system matrix according to the k-space trajectory used in the data collection.

The method achieves the penalty function regularized iterative reconstruction method by using the formula of $$x^* = \underset{\forall x}{\mathrm{argmin}}\{\|Ax - y\|_{L_n}^2 + \lambda_1 R_1(x) + \lambda_2 R_2(x) + \ldots + \lambda_n R_n(x)\}$$

wherein x* is the image after reconstruction, A is the system matrix, x is the image to be reconstructed, y is the raw measurement data, $\|\ \|_{L_n}$ is the n-norm operator, $R_n(\ )$ is the penalty function, λn is the weighted factor, and $$\underset{\forall x}{\mathrm{argmin}}$$

is the minimization optimization operator.

Preferably, the method takes the total variation function as the penalty function.

Preferably, the method calculates Ax using the discrete non-uniform fast Fourier transform algorithm.

Preferably, the method reconstructs the in-phase image and out-of-phase images in parallel.

In the technical solution above, the method further carries out phase correction for the out-of-phase image.

From the above technical solution it can be seen that the present invention reconstructs the in-phase and out-of-phase images by using the penalty function regularized iterative method, which eliminates the need for k-space raw measurement data with 100% sampling rate, so as to reduce the MRI scan time, shorten the entire imaging time, and improve the efficiency of the MRI device. Additionally, in the present invention the process of reconstructing the in-phase image is independent of constructing the out-of-phase image, thus the present invention can rebuild the in-phase image and out-of-phase image in parallel, which further reduces the imaging time and improves the imaging efficiency of the magnetic resonance imaging device.

DESCRIPTION OF THE PREFERRED EMBODIMENTS

Figure 1:
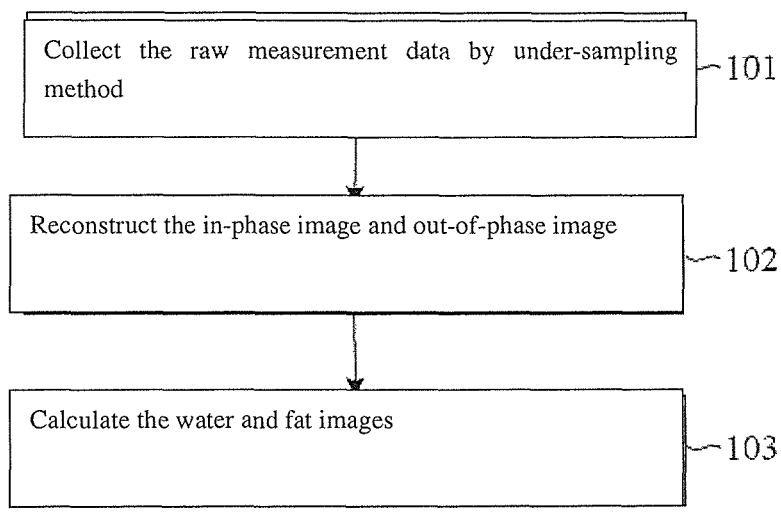
FIG. 1 is a flowchart of the basic steps of the method according to the present invention.

FIG. 1 is a schematic diagram illustrating the flow of one embodiment according to the present invention. In this embodiment, the under-sampling BLADE trajectory is used to acquire k-space raw measurement data, and the water and fat images are calculated based on the three-point Dixon method. However, the present invention is not limited to this technique, and other k-space trajectories can be used to acquire the raw measurement data, and the water and fat images can be calculated based on other algorithms (e.g. two-point Dixon method, etc.).

Referring to FIG. 1, the MRI water-fat separation method according to the embodiment of the present invention includes the following steps:

Step 101, acquiring the raw measurement data of one in-phase image and two out-of-phase images.

In order to understand the present invention easily, the solution of the present invention will be described in detail by using the example of using BLADE trajectory to acquire k-space raw measurement data. It should be noted that the method of the present invention also applies to other k-space trajectories, such as spiral trajectory, radial trajectory, Cartesian trajectory, etc.

The BLADE technology is also referred to as PROPELLER (Periodically Rotated Overlapping Parallel Lines with Enhanced Reconstruction) technology, see the treatise "Motion Correction With PROPELLER MRI: Application to head motion and free-breathing cardiac imaging" (Magnetic Resonance in Medicine, 42: 963-969, November, 1999) by James G. Pipe.

Figure 2A:
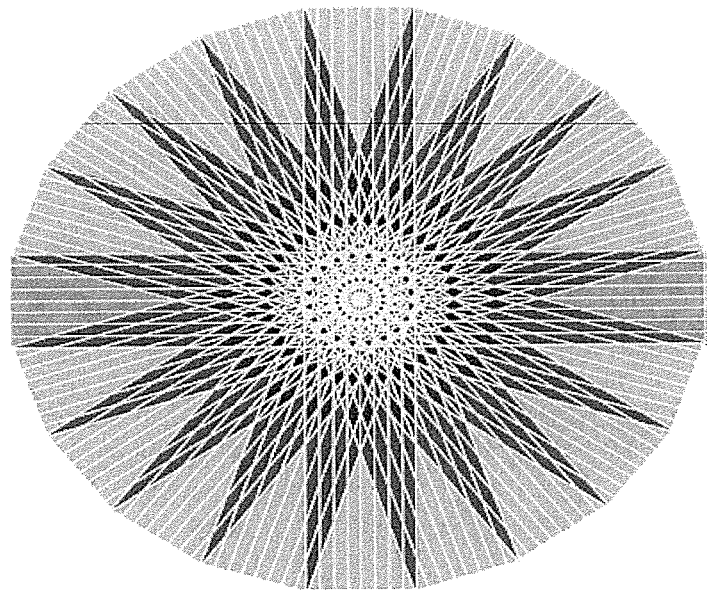
FIG. 2A is a schematic diagram of the conventional BLADE trajectory.

In the conventional BLADE trajectory as shown in FIG. 2A, the k-space data are collected with N (N is a positive integer, N is 10 in FIG. 1) data strips. These data strips are distributed by rotation along the circumference with the same angle, wherein each data strip contains L (L is a positive integer, L is 9 in FIG. 1) rows of parallel data lines. As shown in FIG. 2A, the conventional BLADE trajectory collection has a 100% coverage rate, so it will need a very long scan time.

Figure 2B:
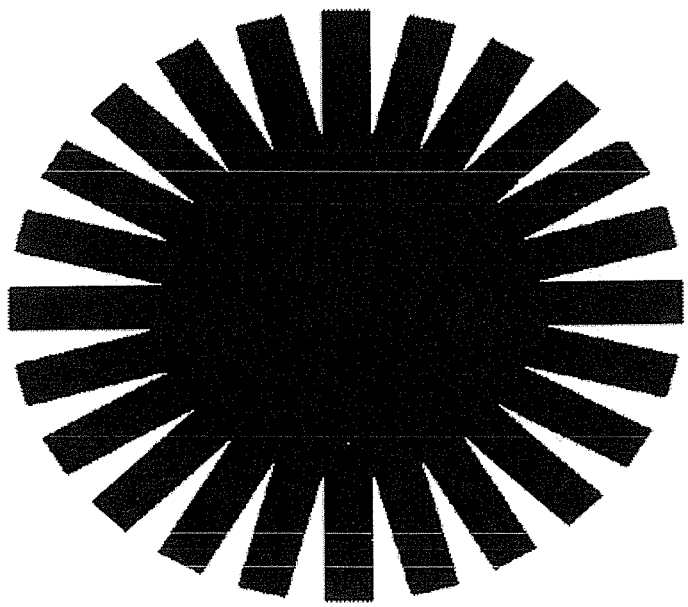
FIG. 2B is a schematic diagram of the under-sampling BLADE trajectory used in the present invention.

As shown in FIG. 2B, the present invention uses an under-sampling acquisition procedure to reduce the time for collecting k-space data. As an example, the under-sampling BLADE trajectory shown in FIG. 2B includes 12 data strips, and there are gaps between these data strips where no data is acquired. The coverage rate of the under-sampling BLADE trajectory shown in FIG. 2B is 52.2%, and compared with the conventional BLADE trajectory shown in FIG. 2A, the under-sampling BLADE trajectory shown in FIG. 2B can save about 52% of scan time accordingly. In addition to the under-sampling BLADE trajectory shown in FIG. 2B, other under-sampling trajectories can also be used to collect k space data according to the method of the present invention.

Figure 3A:
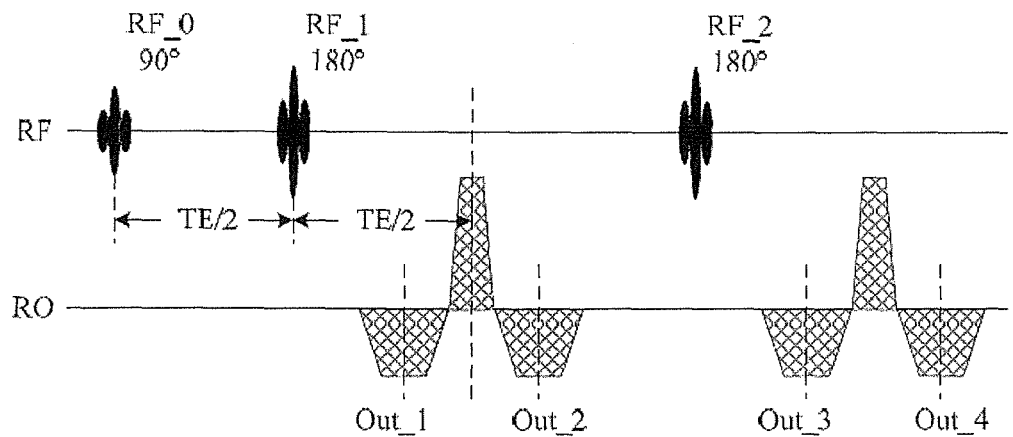
FIG. 3A and FIG. 3B are schematic diagrams showing the sequence of collecting the raw measurement data of the out-of-phase image and the in-phase image using the three-point Dixon method.
Figure 3B:
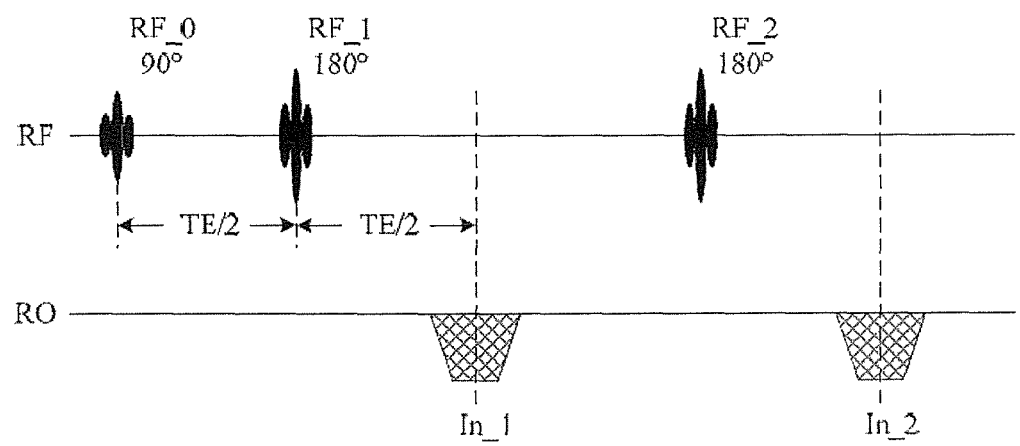

FIG. 3A and FIG. 3B illustrate the sequence when using the three-point Dixon method to collect each data strip in the BLADE trajectory, and in FIG. 3A, the raw measurement data of the out-of-phase image is collected, and in FIG. 3B, the raw measurement data of the in-phase image is collected. In FIG. 3A and FIG. 3B, RF and RO represent radio frequency pulse and readout gradient respectively.

As shown in FIG. 3A, the MRI device first transmits a 90° radio frequency pulse RF_0, and then transmits a 180° rephasing phase radio frequency pulse RF_1. The MRI device applies a readout gradient in the readout gradient direction after the echo time (TE) of the 90° radio frequency pulse RF_0, and reads two data lines Out_1 and Out_2 respectively. Then, the MRI device transmits another 180° rephasing phase radio frequency pulse RF_2 to obtain the second echo, and applies a readout gradient in the readout gradient direction, and reads the two data lines Out_3 and Out_4 respectively; the above operations are repeated until all data lines in the BLADE trajectory are read, to obtain the raw measurement data of two out-of-phase images. The data lines Out_1, Out_3, Out_5 . . . form the raw measurement data of one out-of-phase image, and the data lines Out_2, Out_4, Out_6 . . . form the raw measurement data of another out-of-phase image.

As shown in FIG. 3B, the MRI device transmits a 90° radio frequency pulse RF_0 first, and then transmits a 180° rephasinq radio frequency pulse RF_1. The MRI device applies a readout gradient in the readout gradient direction after the echo time (TE) of the 90° radio frequency pulse RF_0, and reads one data line In_1. Then, the MRI device transmits another 180° rephasinq radio frequency pulse RF_2 to obtain the second echo, and applies a readout gradient in the readout gradient direction, and reads one data line In_2; the above operations are repeated until all data lines in the BLADE trajectory are read to obtain the raw measurement data of one in-phase image.

It should be noted that FIG. 3A and FIG. 3B only illustrate an exemplary acquisition sequence, and are not intended to limit the present invention. For example, according to the present invention, the MRI device can first acquire one in-phase echo, and then acquire two out-of-phase echoes to obtain corresponding raw measurement data. Alternatively, the method acquires one in-phase echo between acquisition of two out-of-phase echoes, and in this way, it acquires three echoes after each rephasing phase pulse, i.e. one in-phase echo and two out-of-phase echoes to obtain corresponding raw measurement data.

In Step 102, the MRI device reconstructs the in-phase image according to the raw measurement data of the in-phase image, and reconstructs the out-of-phase image according to the raw measurement data of the out-of-phase image. That is, the in-phase image and the out-of-phase image are reconstructed independently, which is different from the Chinese patent application described in the Background Technology section.

The present invention combines the penalty function regularized iterative reconstruction method with the Dixon water-fat separation calculation, and this penalty function regularized iterative reconstruction method is an optimization operation, which can be expressed by Formula (1).

$$x^* = \underset{\forall x}{\operatorname{argmin}}\{\|Ax - y\|_{Ln}^2 + \lambda_1 R_1(x) + \lambda_2 R_2(x) + \ldots + \lambda_n R_n(x)\} \quad (1)$$

wherein x* is the image after reconstruction. A is the system matrix, and can be a linear operator, or a non-linear operator. The present invention generates the system matrix A according to the actual k-space trajectory, for example, generating the system matrix A according to the under-sampling according to the present invention's BLADE trajectory in Step 101 in this embodiment. x is the image to be reconstructed. y is the raw measurement data which is collected. $\|\ \|_{Ln}$ is the n-norm (such as 2-norm) operator. $R_n(\ )$ is the penalty function, which is weighted by scalar factor $\lambda n$. Usually, the penalty function can be selected freely to meet the need of image reconstruction. In this embodiment, the total variation (VT) function is used as the penalty function. Operator $$\underset{\forall x}{\operatorname{argmin}}$$

is the minimization optimization operator, and this operator minimizes norm and penalty function through iteration steps to calculate the solution of x. In addition, the matrix operation Ax can be replaced by other numerical functions, to optimize the algorithm. In this embodiment, the discrete non-uniform fast Fourier transform (NUFFT) algorithm is used, and this algorithm can be implemented by Matlab® software from MathWorks Company.

On the basis of the algorithm of above Equation (1), preferably, the present invention uses the parallel calculation to reconstruct one in-phase image and two out-of-phase images in parallel by using the three-point Dixon method, thereby further reducing the time used and improving the imaging speed.

Figure 4:
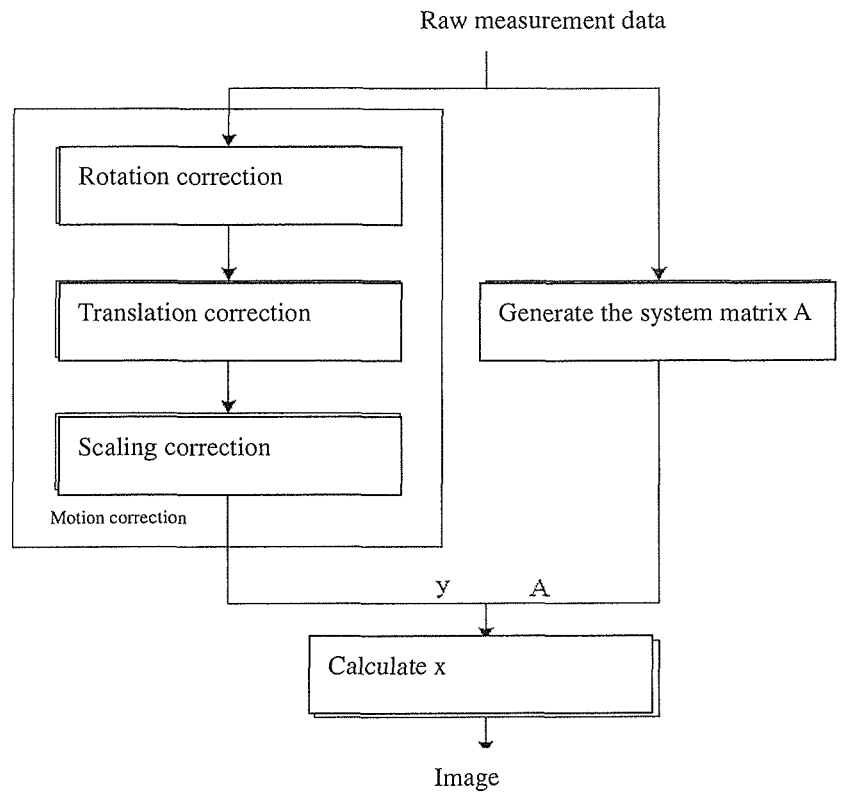
FIG. 4 is a schematic diagram showing the flow of a method according to the present invention for reconstructing the in-phase image and the out-of-phase image.

FIG. 4 shows a method according to the present invention for reconstructing the in-phase image and the out-of-phase image. Taking reconstructing the out-of-phase image as an example, as shown in FIG. 4, the process of reconstructing an out-of-phase image includes the following steps: carrying out the motion correction for the raw measurement data of the out-of-phase image, including rotation correction, translation correction and scaling correction, to obtain y in the Equation (1). The scaling correction is introduced here to correct the tissue expansion and shrinkage motion of some parts, such as the abdominal motion caused by respiratory motion. While carrying out the above motion correction, the system matrix A is generated according to the k-space trajectory used in the data collection. Then, the equation y=Ax is solved according to Equation (1) by using the iteration method, to obtain the out-of-phase image x.

When reconstructing one in-phase image and two out-of-phase images as described above, the MRI device can reconstruct these images independently and in parallel by using different threads according to the present invention, which can further reduce the time used in water-fat separation imaging, and can improve imaging speed and the efficiency of the MRI device.

In Step 103, the water image and fat image are calculated according to the in-phase image and out-of-phase image obtained by the reconstruction above.

Figure 5:
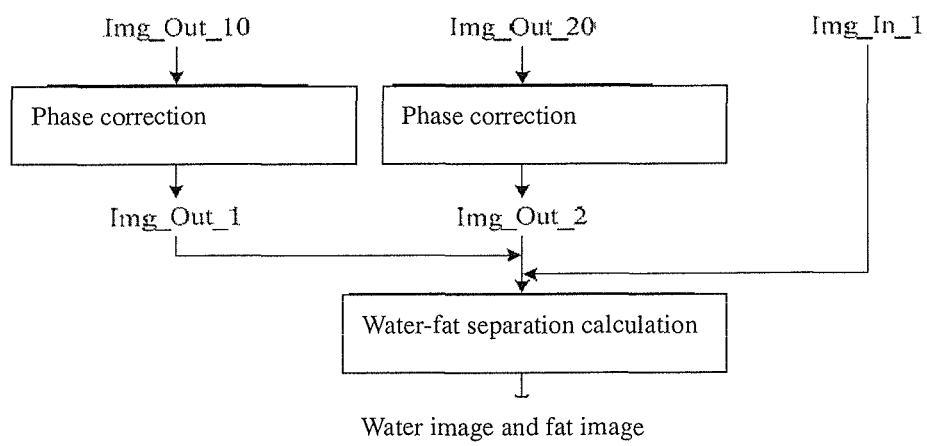
FIG. 5 is a schematic diagram showing the flow of carrying out water-fat separation calculation from the in-phase image and the out-of-phase image according to the method of the present invention.

FIG. 5 is a schematic diagram showing how water-fat separation calculation is conducted from the in-phase image and the out-of-phase image according to the method of the present invention. After the reconstruction shown in FIG. 4, two out-of-phase images Img_Out_10 and Img_Out_20 and one in-phase image Img_In_1 are obtained. The phase correction is performed for the out-of-phase images Img_Out_10 and Img_Out_20 respectively, to eliminate the artifacts caused by inhomogeneity of the magnetic field, and obtain the corrected out-of-phase images Img_Out_1 and Img_Out_2, respectively. Then the final water image Img_Water and fat image Img_Fat are calculated according to Formulas (2) and (3) using the in-phase image Img_In_1 and the out-of-phase images Img_Out_1, Img_Out_2.

Img_Water=Img_In_1+(Img_Out_1+Img_Out_2)/2 (2)

Img_Fat=Img_In_1−(Img_Out_1+Img_Out_2)/2 (3)

It should be noted that the present invention is not limited to the calculation method shown in Equations (2) and (3), and other water-fat separation methods can be used according to specific needs.

Figure 6A:
FIG. 6A and FIG. 6D are respectively the fat image and water image obtained according to the method of the present invention.
Figure 6B:
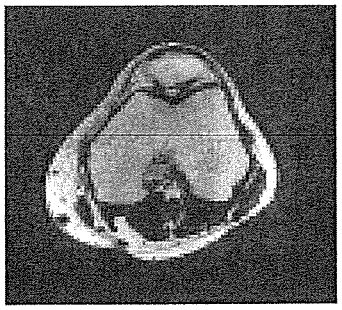
FIG. 6B and FIG. 6E are respectively the fat image and water image obtained according to the conventional gridding reconstruction method.
Figure 6C:
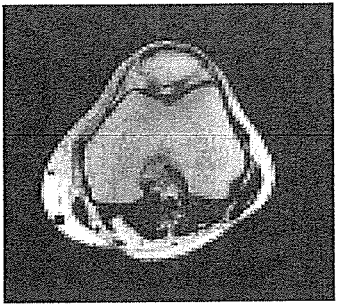
FIG. 6C and FIG. 6F are respectively the fat image and water image obtained according to the fast spin echo (TSE) Dixon sequence collection and Dixon reconstruction.
Figure 6D:
Figure 6E:
Figure 6F:
Figure 6G:
FIG. 6G is the water image obtained according to the standard TSE sequence collection and fat saturation (FatSat) technology.

The present invention also compares the water and fat images obtained from various methods. FIG. 6A to FIG. 6G show the water and fat images obtained according to different methods respectively. Among these, FIGS. 6A, 6B and 6C are fat images, and FIGS. 6D, 6E, 6F and 6G are water images. In FIGS. 6A and 6D, the TSE BLADE Dixon sequence under-sampling method is used to acquire k-space raw measurement data, and the iterative reconstruction method with the total variation function as the penalty function described above is used. In FIGS. 6B and 6E, the TSE BLADE Dixon sequence and the conventional gridding sampling are used to collect k-space data, and the conventional gridding reconstruction method is used. In FIGS. 6C and 6F, the Cartesian trajectory TSE Dixon sequence is used to acquire k-space raw measurement data, and the conventional Dixon reconstruction method is used. In FIG. 6G, the standard TSE sequence is used to acquire k-space raw measurement data, and the fat saturation (FatSat) method is used to rebuild the water image.

As compared with the images (FIGS. 6B, 6C, 6E, 6F, 6G) obtained by other methods, the method of the present invention can correctly separate the water and fat images (FIGS. 6A and 6D). In the fat images, obvious strip artifacts can be seen in FIG. 6B, and pulsative artifacts can be seen in FIG. 6C; in the water images, pulsative artifacts also can be seen in FIG. 6G. In addition, in the water images, FIG. 6D can show more details than FIG. 6E, and the results of FIG. 6F and FIG. 6G are similar to the result of FIG. 6D. From the above comparison, we can see that the method of the present invention can not only reduce the scanning time remarkably, but can also ensure the water-fat separation quality and the image quality.

Although modifications and changes may be suggested by those skilled in the art, it is the intention of the inventor to embody within the patent warranted hereon all changes and modifications as reasonably and properly come within the scope of his contribution to the art.

We claim as our invention:

1. A magnetic resonance (MR) imaging water-fat separation method, comprising the steps of:
   operating an MR data acquisition device with a data acquisition sequence that causes separated in-phase image raw measurement data and out-of-phase image raw measurement data to be acquired;
   entering said in-phase image raw measurement data and said out-of-phase raw image measurement data into an electronic memory representing k-space according to a k-space trajectory, with undersamplinq of k-space that causes less than an entirety of k-space to be filled with said in-phase image raw measurement data and said out-of-phase image raw measurement data;
   in computer, generating a system matrix according to said k-space trajectory;
   in said computer, reconstructing an in-phase image and an out-of-phase image from said in-phase and out-of-phase raw measurement data using a penalty function regularized iterative reconstruction; algorithm that embodies sad system matrix; and
   in said computer, calculating a water image and a fat image from said in-phase image and out-of-phase image, and making said water image and said fat image available at an output of said computer in electronic form, as respective data files.

2. The method as claimed in claim 1 comprising acquiring the raw measurement data by said under-sampling along a k-space trajectory selected from the group consisting of a spiral trajectory, a radial trajectory, a Cartesian trajectory and a BLADE artifact correction trajectory.

3. The method as claimed in claim 1, comprising acquiring the raw measurement data of one in-phase image and two out-of-phase images, and reconstructing one in-phase image and two out-of-phase images.

4. The method as claimed in claim 3, comprising first acquiring two out-of-phase echoes, and then acquiring one in-phase echo.

5. The method as claimed in claim 3, comprising first acquiring one in-phase echo, and then acquiring two out-of-phase echoes.

6. The method as claimed in claim 3, comprising first acquiring a first out-of-phase echo, and then acquiring one in-phase echo, and then acquiring a second out-of-phase echo.

7. The method as claimed in claim 1, comprising using $$x^* = \operatorname*{argmin}_{\forall x}\{\|Ax - y\|_{Ln}^2 + \lambda_1 R_1(x) + \lambda_2 R_2(x) + \ldots + \lambda_n R_n(x)\}$$

as said penalty regularized interactive reconstruction algorithm, wherein x* is the image after reconstruction, A is the system matrix, x is the image to be reconstructed, y is the raw measurement data, $\|\|_{Ln}$ is the n-norm operator, $R_n(\ )$ is the penalty function, λn is the weighted factor, and $$\operatorname*{argmin}_{\forall x}$$

is the minimization optimization operator.

8. The method as claimed in claim 5, comprising using a total variation function as the penalty function.

9. The method as claimed in claim 5, comprising calculating Ax using a discrete non-uniform fast Fourier transform algorithm.

10. The method as claimed in claim 1 comprising reconstructing said in-phase image and out-of-phase image in parallel.

11. The method as claimed in claim 1, comprising implementing phase correction of the out-of-phase image.

* * * * *